United States Patent [19]

Jautelat et al.

[11] 4,358,598
[45] Nov. 9, 1982

[54] 2-(2,2-DIMETHYL-3-BUTEN-1-YL)-2-OXAZO-LINES

[75] Inventors: Manfred Jautelat, Burscheid; Dieter Arlt, Cologne, both of Fed. Rep. of Germany

[73] Assignee: Bayer Aktiengesellschaft, Leverkusen, Fed. Rep. of Germany

[21] Appl. No.: 212,051

[22] Filed: Dec. 1, 1980

Related U.S. Application Data

[62] Division of Ser. No. 15,376, Feb. 26, 1979, Pat. No. 4,283,554.

[30] Foreign Application Priority Data

Mar. 15, 1978 [DE] Fed. Rep. of Germany ....... 2811190

[51] Int. Cl.³ .......................................... C07D 263/10
[52] U.S. Cl. .................................. 548/216; 548/217; 548/237
[58] Field of Search ....................... 548/216, 217, 237

[56] References Cited

U.S. PATENT DOCUMENTS 2,892,837  6/1959  de Stevens et al. ................. 548/217
4,087,611  5/1978  Raghu et al. ........................ 548/237

FOREIGN PATENT DOCUMENTS 2319643  2/1977  France ................................ 548/216

Primary Examiner—Anton H. Sutto
Attorney, Agent, or Firm—Sprung, Horn, Kramer & Woods

[57] ABSTRACT

A process comprising reacting a 2-methyloxazoline of the formula

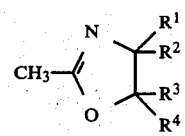

(VI)

in which
R¹, R², R³ and R⁴ each independently is hydrogen, alkyl, aralkyl, optionally substituted aryl or two of them together form a ring,
with a 3-methyl-2-buten-1-yl derivative of the formula

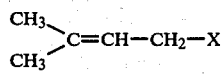

(VII)

in which
X is halide, sulphonate or phosphate, thereby to produce a 2-methyl-3-(3-methyl-2-butenyl)-2-oxazolinium salt of the formula

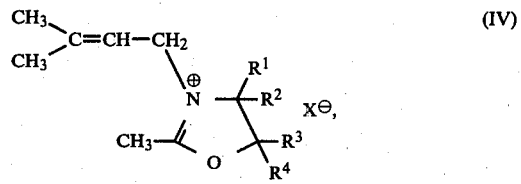

(IV)

reacting the oxazolinium salt with an alcoholate of the formula $$R^5\text{—O—M}$$ (V)

in which
M is one equivalent of an alkali metal or alkaline earth metal cation,
to produce an oxazolidine of the formula

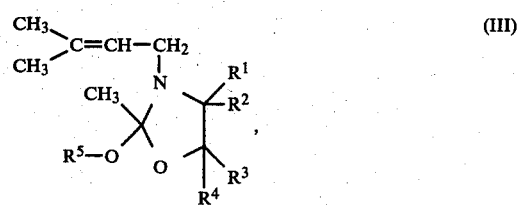

(III)

pyrolyzing the oxazolidine to produce a 2-methylene-3-(3-methyl-2-butenyl)-oxazolidine of the formula

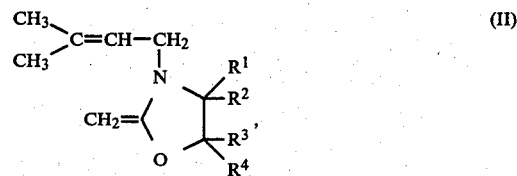

(II)

and heating the 2-methylene-3-(3-methyl-2-butenyl)-oxazolidine to produce a 2-(2,2-dimethyl-3-buten-1-yl)-2-oxazoline of the formula

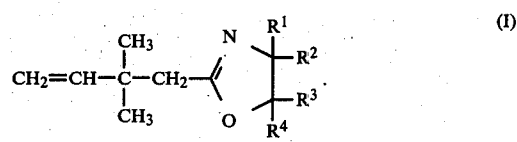

(I)

The compounds (II), (III) and (IV) are new.

1 Claim, No Drawings

2-(2,2-DIMETHYL-3-BUTEN-1-YL)-2-OXAZOLINES

This is a division of Application Ser. No. 15,376, filed Feb. 26, 1979 now U.S. Pat. No. 4,283,544.

The present invention relates to an unobvious process for the preparation of certain 2-(2,2-dimethyl-3-buten-1-yl)-2-oxazolines. These compounds can be used as intermediates for the preparation of insecticides, for example 2-(2,2-dichlorovinyl)-3,3-dimethyl-cyclopropanecarboxylic acid 3-phenoxy-benzyl ester.

2-(2,2-Dimethyl-3-buten-1-yl)-oxazolines can be obtained from 3,3-dimethyl-4-pentenoic acid and derivatives thereof by reaction with ethanolamines (Application Ser. No. 920,031, filed June 28, 1978, now pending. However, since 3,3-dimethyl-4-pentenoic acid and derivatives thereof are available only by multi-stage synthesis processes, this preparation route for 2-(2,2-dimethyl-3-buten-1-yl)-oxazolines is very expensive.

It has now been found that a 2-(2,2-dimethyl-3-buten-1-yl)-2-oxazoline of the general formula

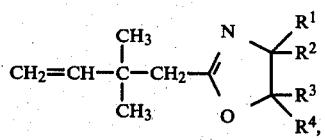
(I)

in which
$R^1$, $R^2$, $R^3$ and $R^4$, independently of one another, each represent hydrogen, alkyl, aralkyl, optionally substituted aryl or parts of a ring,
is obtained when a 2-methylene-3-(3-methyl-2-butenyl-)oxazolidine of the general formula

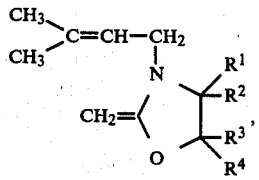
(II)

in which
$R^1$–$R^4$ have the above-mentioned meanings, is heated, optionally in the presence of a diluent.

The 2-methylene-3-(3-methyl-2-butenyl)-oxazolidines of the formula (II) have not been described in the literature; they are obtained however by a process in which oxazolidines of the general formula

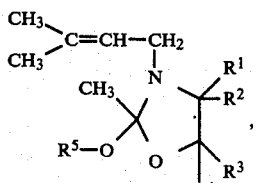
(III)

in which
$R^1$–$R^4$ have the meanings stated above and
$R^5$ represents alkyl or aryl, are subjected to pyrolysis in the liquid phase or gas phase in the presence or absence of an inert diluent.

Furthermore, it has been found that a 2-(2,2-dimethyl-3-buten-1-yl)-2-oxazoline of the formula (I) can also be obtained by a process in which an oxazolidine of the general formula

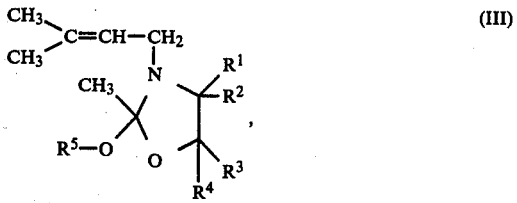
(III)

in which
$R^1$–$R^5$ have the meanings stated above, is subjected to pyrolysis in the liquid phase or gas phase in the presence or absence of an inert diluent.

The oxazolidines of the formula (III) have not been described in the literature. They are obtained by a process in which 2-methyl-3-(3-methyl-2-butenyl)-2-oxazolinium salts of the general formula

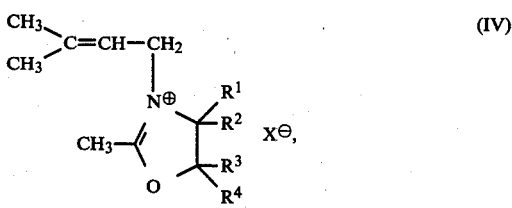
(IV)

in which
$R^1$, $R^2$, $R^3$ and $R^4$ have the above meanings and
X represents halogen, sulphonate or phosphate, are reacted with alcoholates of the general formula

$$R^5\text{—O—M} \qquad (V)$$

in which
M represents one equivalent of an alkali metal cation or alkaline earth metal cation and
$R^5$ represents alkyl or aryl.

The 2-methyl-3-(3-methyl-2-butenyl)-2-oxazolinium salts of the general formula (IV) have not been described in the literature. They are obtained by a process in which 2-methyloxazolines of the general formula

(VI)

in which
$R^1$–$R^4$ have the above meanings,
are reacted with 3-methyl-2-buten-1-yl derivatives of the general formula

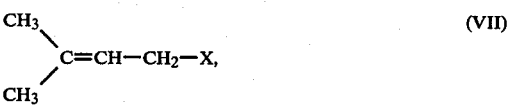
(VII)

in which
X has the above meaning.

The pyrolysis of the oxazolidines of the formula (III) leads to the 2-methylene-3-(3-methyl-3-butenyl)-oxazolidines of the formula (II), which rearrange to give the 2-oxazolines of the general formula (I). The selective course of this reaction was surprising, since attempts to carry out this reaction using a basic catalyst analogously to known reactions lead to polymeric products (see Chem. Ber. 97, 3,081 (1964) and Liebigs Ann. Chem. 641, 1 (1961)).

It is also surprising that the reaction of the oxazolinium salts of the formula (IV) with alcoholates of the formula (V) does not lead, by ring opening, to acetamides of the formula (VIII)

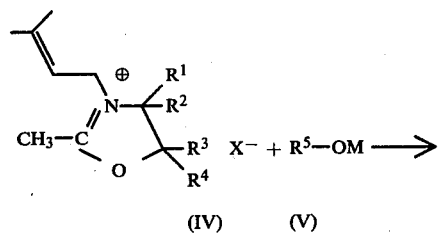

(IV)    (V)

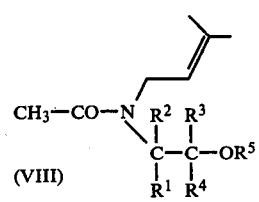

(VIII)

as was to be assumed on the basis of similar reactions with pyridine (J. Macrom. Sci. Chem. 1972, 1,631)

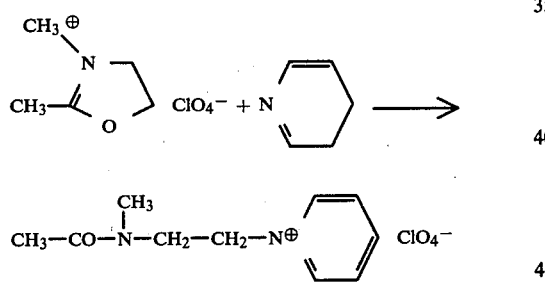

but leads selectively, by addition, to the hitherto unknown 2-alkoxy-2-methyl-3-(3-methyl-2-butenyl)-oxazolidines, or the 2-aryloxy analogues.

The process for the preparation of the oxazolines of the formula (I) has the advantage that the starting materials used therefor can be prepared from readily available and inexpensive substances, such as, for example, 2-methyl-oxazoline and isoprene.

If 2-methylene-3-(3-methyl-2-butenyl)-oxazolidine is used as the starting material, the course of the reaction can be represented by the equation which follows:

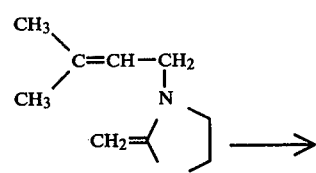

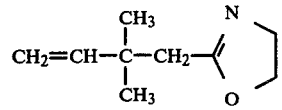

If 2-methoxy-2-methyl-(3-methyl-2-butenyl)-oxazolidine is used as the starting material and the reaction is carried out without isolating 2-methylene-3-(3-methyl-2-butenyl)-oxazolidine, the course of the reaction can be represented by the equation which follows:

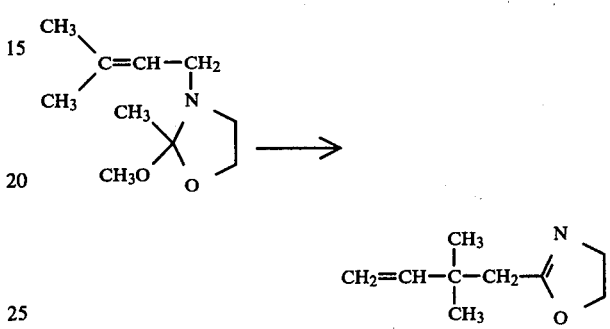

The preparation of 2-methoxy-2-methyl-(3-methyl-2-butenyl)-oxazolidine by reacting 2-methyl-3-(3-methyl-2-butenyl)-2-oxazolinium bromide with sodium methylate can be represented by the equation which follows:

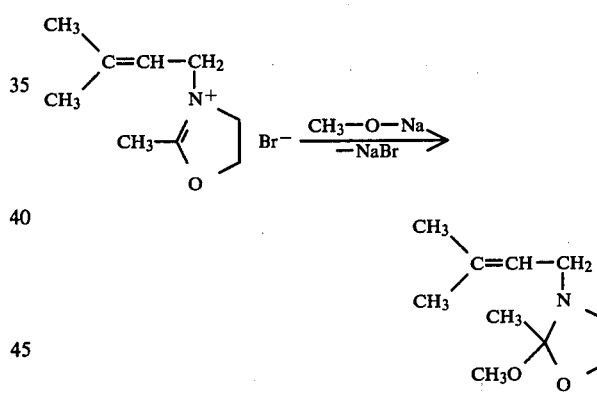

The preparation of 2-methyl-3-(3-methyl-2-butenyl)-2-oxazolinium bromide from 2-methyl-2-oxazoline and 3-methyl-2-butenyl bromide can be represented by the equation which follows:

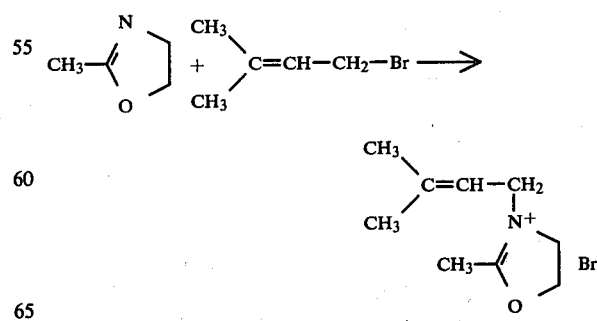

If 2-methyl-2-oxazoline and 3-methyl-2-butenyl bromide (prenyl bromide) are used as starting materials, the course of the reaction can be represented by the equation which follows:

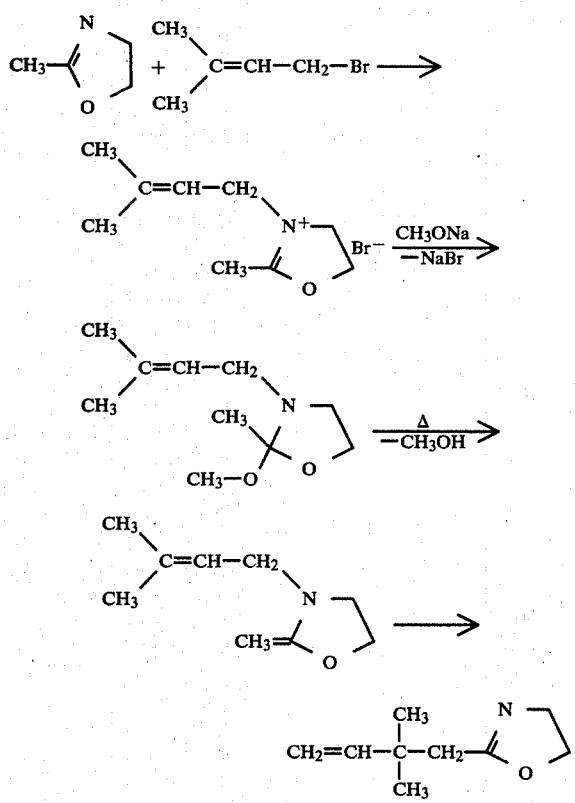

The formula (II) provides a general definition of the 2-methylene-3-(3-methyl-2-butenyl)-oxazolidines. $R^1$, $R^2$, $R^3$ and $R^4$ independently of one another preferably represent hydrogen, alkyl radicals with 1-4 carbon atoms, aralkyl radicals with 7-9 carbon atoms or aryl, for example phenyl, which is optionally substituted by halogen, alkoxy with 1-4 carbon atoms or phenoxy.

$R^1$ and $R^2$ and/or $R^3$ and $R^4$ can alternatively form an alkylene chain with 4-6 carbon atoms. $R^1$ can also form an alkylene chain of 3-4 carbon atoms with $R^3$ or $R^4$.

Examples which may be mentioned of the 2-methylene-3-(3-methyl-2-butenyl)-oxazolidines which can be used according to the invention are those obtainable by the above-mentioned reactions from the 2-methyl-2-oxazolines which follow: 2-methyl-2-oxazoline, 2,4,4,-trimethyl-2-oxazoline, 2,5,5-trimethyl-2-oxazoline, 2,4,4,5,5-pentamethyl-2-oxazoline, 5-benzyl-2-methyl-2-oxazoline, 2-methyl-4,4-tetramethylene-2-oxazoline, 2-methyl-4,5-tetramethylene-2-oxazoline, 2-methylbenzoxazole, 2-methyl-4-phenyl-2-oxazoline, 2-methyl-5-phenyl-2-oxazoline, 2-methyl-5-(m-phenoxyphenyl)-2-oxazoline and 2-methyl-5-pentafluorophenyl-2-oxazoline.

The formula (VII) provides a general definition of the 3-methyl-2-buten-1-yl derivatives which can be used, in the above-mentioned reactions, for the preparation of the 2-methylene-3-(3-methyl-2-butenyl)-oxazolidines which can be used according to the invention. X preferably represents chloride, bromide, iodide, methanesulphonate, p-toluenesulphonate or benzenesulphonate.

The formula (V) provides a general definition of the alcoholates which likewise can be used, in the above-mentioned reactions, for the preparation of the 2-methylene-3-(3-methyl-2-butenyl)-oxazolidines which can be used according to the invention. $R^5$ preferably represents alkyl radicals with 1-4 carbon atoms or aryl, such as phenyl. M preferably represents sodium, potassium, magnesium or calcium. Examples which may be mentioned are: sodium methylate, sodium ethylate, sodium propylate, sodium butylate, potassium methylate, magnesium methylate and calcium methylate.

The preparation of the oxazolinium salts of the formula (IV) can be carried out either in the presence or in the absence of an inert diluent at a temperature from about 0°–80° C., preferably about 20°–60° C. Possible diluents are, inter alia, hydrocarbons, such as benzine, toluene, chloroform, methylene chloride and 1,2-dichloroethane; ethers, such as diethyl ether and dioxane; alcohols, such as methanol, ethanol and butanol; acetonitrile or dimethylformamide.

The reaction of the oxazolinium salts of the formula (IV) with alcoholates of the formula (V) can be carried out either using isolated oxazolinium salts, in a separate process step, or after the preparation of the oxazolinium salts, in a one-pot reaction. Possible solvents are alcohols, such as methanol, ethanol and butanol, and also inert diluents, such as hydrocarbons, for example, toluene, methylene chloride or chlorobenzene, ethers, for example diethyl ether, tetrahydrofuran, dioxane or dimethoxyethane, and also dimethylsulphoxide, dimethylformamide, hexamethylphosphoric acid triamide or acetonitrile. The reaction is carried out at a temperature from about 70° to 100° C., preferably about 50° to 60° C.

The preparation of the 2-(2,2-dimethyl-3-buten-1-yl)-2-oxazolines is then preferably carried out, without isolating the 2-methylene-3-(3-methyl-2-butenyl)-oxazolidines arising as an intermediate stage, by pyrolysis of the oxazolidines of the formula (III).

The pyrolysis of the oxazolidines of the formula (III) can be carried out in the gas phase by a process in which the vapors are passed, in a stream of inert gas, such as nitrogen, through a heated tube, which is packed with inert heat transfer bodies, such as glass balls, under pressure or under normal pressure and are then condensed. Alternatively, the oxazolidine is vaporized under reduced pressure and these vapors are passed through a heated tube for the splitting reaction.

Pyrolysis in the liquid phase is also possible. A solution of the oxazolidines in an inert diluent is heated, or the solution is dripped onto a heat transfer body at suitable temperatures. The temperature of the pyrolysis and rearrangement can be varied within a substantial range. In general, the process is carried out at temperatures of about 200° to 500° C., preferably at about 300° to 400° C. Suitable diluents are all the inert solvents, such as hydrocarbons, for example toluene, xylene, cyclohexane, decalin and quinoline, or ethers, such as dioxane and diphenyl ether.

The reactants are preferably employed in equimolar amounts in the individual process stages up to the preparation of the compound (III). Nevertheless, deviations therefrom, one component being employed in more or less than the equimolar amount, are possible.

The Examples which follow illustrate the process according to the invention, and the preparation of the starting materials and precursors.

EXAMPLE 1

8.5 g (0.1 mol) of 2-methyloxazoline and 14.9 g (0.1 mol) of 3-methyl-2-butenyl bromide (prenyl bromide) were stirred at 20°–25° C. for 2 hours, crystalline, hygroscopic 2-methyl-3-(3-methyl-2-butenyl)-2-oxazolinium bromide being formed in an exothermic reaction.

NMR (CDCl₃): δ1.7–1.9 (m, 6H); 2.7 (s, 3H); 4.2–4.4 (m, 4H); 5.15 (d, 2H) and 5.5 (t, 1H)

EXAMPLE 2

23.4 g (0.1 mol) of 2-methyl-3-(3-methyl-2-butenyl)-2-oxazolinium bromide were stirred with 22 ml of a 5 N sodium methylate solution at 40° C. for 1 hour, the sodium chloride which had precipitated was separated off and the product phase was washed with absolute ether and concentrated on a rotary evaporator. The liquid which remained distilled at a boiling point 96°–98° C./20 mm Hg; 15.2 g (82 mmols, 82%) of 2-methoxy-2-methyl-3-(3-methyl-2-butenyl)-oxazolidine.

NMR (CDCl₃): δ1.35 (s, 3H); 1.6–1.75 (m, 6H), 2.8–3.25 (m, 4H); 3.2 (s, 3H); 3.8–4.1 (m, 2H) and 5.25 (t, 1H).

EXAMPLE 3

18.5 g (0.1 mol) of 2-methoxy-2-methyl-3-(3-methyl-2-butenyl)-oxazolidine were distilled under a pressure of 20 mbars and the vapors were passed through a tube, packed with glass balls and heated to 400° C., and then condensed. 2-(2,2-Dimethyl-3-butenyl)-2-oxazoline was found in a yield of 86% in the 16.8 g of condensate, the conversion being 73%. The pure product (boiling point 78°–80° C./14 mm Hg) was isolated by fractional distillation.

NMR (CDCl₃): 1.1 (s, 6H); 2.3 (s, 2H); 3.7–4.4 (m, 4H) and 4.8–6.2 (3H, —CH=CH₂)

EXAMPLE 4

9.25 g (50 mmols) of 2-methoxy-2-methyl-3-(3-methyl-2-butenyl)-oxazolidine, as a 10% strength solution in toluene, were dropped in a stream of nitrogen onto glass balls, heated to 350° C., in a heated tube and subsequently condensed. The condensate was freed from the solvent and the residue was distilled at boiling point 80°–82° C./18 mm Hg. 6.0 g (39 mmols, 78%) of 2-(2,2-dimethyl-3-butenyl)-2-oxazoline, which was identical to the above product (Example 3), were obtained.

EXAMPLE 5

8.5 g (0.1 mol) of 2-methyloxazoline and 14.9 g (0.1 mol) of 3-methyl-2-butenyl bromide were stirred in 50 ml of acetonitrile at 20° to 25° C. for 2 hours and, after adding 20 ml of a 5 N sodium methylate solution, the mixture was stirred at room temperature for a further 3 hours. The solution was filtered and, after stripping off the solvent, the residue was distilled. 15.6 g (84 mmols, 84%) of 2-methoxy-2-methyl-3-(3-methyl-2-butenyl)-oxazolidine of boiling point 96°–99° C./20 mm Hg were obtained.

EXAMPLE 6

The same reaction as in Example 5 in 50 ml of methylene chloride gave the above oxazolidine in a yield of 79%.

EXAMPLE 7

8.5 g (0.1 mol) of 2-methyloxazoline and 14.9 g (0.1 mol) of prenyl bromide were stirred in 50 ml of n-hexane at 40° C. for 1 hour, whereupon a suspension formed, which, after adding 0.11 mol of a sodium ethylate solution in ethanol, was again stirred at 40° C. for 1 hour. The solution was filtered, the filtrate was concentrated on a rotary evaporator and the residue was distilled using an oil pump. 12.3 g (0.062 mol, 62%) of 2-ethoxy-2-methyl-3-(3-methyl-2-butenyl)-oxazolidine were isolated at a boiling point 67° C./0.1 mm Hg.

EXAMPLE 8

10 g (50 mmols) of 2-ethoxy-2-methyl-3-(3-methyl-2-butenyl)-oxazolidine were dropped in a stream of nitrogen onto glass balls, heated to 325° C., in a heated tube and the vapors were condensed in a connected condenser. The alcohol was removed in vacuo and the 2-(2,2-dimethyl-3-butenyl)-2-oxazoline which remained was distilled at a boiling point 76°–78° C./17 mm Hg (6.5 g; 42.5 mmols, 85%).

EXAMPLE 9

14.9 g (0.1 mol) of prenyl bromide and 8.5 g (0.1 mol) of 2-methyl-oxazoline were stirred in 50 ml of methylene chloride at 25° C. for 2 hours and the mixture was treated with 0.11 mol of a sodium butylate solution in n-butanol at 40° C. for 1 hour and worked up in the customary manner. 13.4 g (59 mmols, 59%) of 2-butoxy-2-methyl-3-(3-methyl-2-butenyl)-oxazolidine were obtained by distillation at a boiling point 78°–80° C./0.3 mm Hg.

EXAMPLE 10

Pyrolysis of 11.4 g (50 mmols) of 2-butoxy-2-methyl-3-(3-methyl-2-butenyl)-oxazolidine at 400° C. according to Example 8 gave 2-(2,2-dimethyl-3-butenyl)-2-oxazoline in 70% yield.

EXAMPLE 11

Pyrolysis of 30 g (0.162 mol) of 2-methoxy-2-methyl-3-(3-methyl-2-butenyl)-oxazolidine in a stream of nitrogen at 325° C. without a diluent gave 88% of 2-(2,2-dimethyl-3-butenyl)-2-oxazoline.

EXAMPLE 12

226 g (2 mols) of 2,4,4-trimethyloxazoline were dropped at room temperature to 298 g (2 mols) 3-methyl-2-butenyl bromide in 400 ml absolute methylenchloride and were stirred for 12 hours at 20° C. After cooling to 0° C. 400 ml (2 mols) of a 30% solution of sodium methylate were added and the mixture was stirred for a further hour at room temperature. The solution was filtered and after removing off the solvent the residue was distilled. 368 g (1.72 mols, 86%) of 2-methoxy-3-(3-methyl-2-butenyl)-2,4,4-trimethyloxazolidine of boiling point 70°–76° C./0.05 mm Hg were obtained. NMR (CDCL₃): α1.1 (s, 3H); 1.2 (s, 3H); 1.4 (s, 3H); 1.6–1.7 (bs, 6H); 3.2 (s, 3H); 3.25 (d,J=6.5 Hz, 2H); 3.65 (s, 2H); 5.25 (t, J=6.5 Hz, 1H).

EXAMPLE 13

The solution of oxazoliniumbromide prepared as in the first step of Example 12 was cooled to −70° C. 400 ml (2 mols) of a 30% solution of sodium methylate were dropped in slowly. The mixture was stirred for a further hour at room temperature. The solution was filtered and, after removing of the solvent, slowly distilled. 282 g (1.56 mols, 78%) 4,4-dimethyl-2-methylene-3(3-methyl-2-butenyl)-oxazolidine of boiling point 56°–60° C./0.1 mm Hg were obtained.

NMR (CDCl₃): α1.1 (s, 3H); 1.15 (s, 3H); 1.7 (bs, 6H); 3.15 (AB, 2H), 3.5 (d, J=6 Hz, 2H); 3.8 (s, 2H); 5.25 (t, J=6 Hz, 1H).

EXAMPLE 14

246 g (1.15 mols) 2-methoxy-3-(3-methyl-2-butenyl)-2,4,4-trimethyloxazolidin were pyrolized according to Example 8. 170 g (0.94 mols, 81%) 2-(2,2-dimethyl-3-butenyl)-4,4-dimethyl-2-oxazolidine of a boiling point of 84°–92° C./20 mm Hg were obtained.

NMR (CDCl$_3$): α1.1 (s, 6H); 1.25 (s, 6H); 2.25 (s, 2H); 3.85 (s, 2H); 4.85–6.15 (—CH=CH$_2$).

It will be appreciated that the instant specification and examples are set forth by way of illustration and not limitation, and that various modifications and changes may be made without departing from the spirit and scope of the present invention.

We claim:

1. A 2-methyl-3-(3-methyl-2-butenyl)-2-oxazolinium salt of the formula

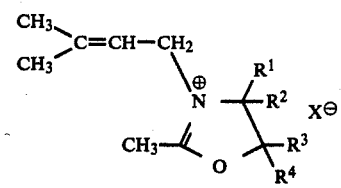

in which

R$^1$, R$^2$, R$^3$ and R$^4$ each independently is hydrogen, alkyl, aralkyl, optionally substituted aryl or two of them together form an alkylene chain with 4–6 carbon atoms, and X is halogen, sulphonate or phosphate.

* * * * *